United States Patent [19]

Heim

[11] Patent Number: 4,891,209

[45] Date of Patent: Jan. 2, 1990

[54] INTERNATIONAL NON-STICK CHEWING MATERIAL

[76] Inventor: Moses L. Heim, Casablanca Hotel 6345 Collins Ave., Miami Beach, Fla. 33141

[21] Appl. No.: 247,362

[22] Filed: Sep. 21, 1988

[51] Int. Cl.$^4$ .............................................. A61K 9/68
[52] U.S. Cl. ...................... 424/48; 424/435; 426/3; 426/5; 514/900; 514/953
[58] Field of Search ............ 424/48, 435; 426/3, 426/5; 514/900, 953

[56] References Cited

U.S. PATENT DOCUMENTS 4,554,154 11/1985 White ................................. 424/16

Primary Examiner—Ellis P. Robinson
Assistant Examiner—P. J. Ryan
Attorney, Agent, or Firm—Fleit, Jacobson, Cohn, Price, Holman & Stern

[57] ABSTRACT

A chewing material or items constructed of latex material. In one embodiment of the invention, the latex chewing material is constructed to simulate the size and shape of a stick of conventional chewing gum. The latex material will not deteriorate when being chewed and while not intended to be ingested, it is constructed of non-toxic material and is not harmful if swallowed. The latex chewing material will not stick to any surface or any other item. The material is not water soluble and is sugar free and salt free. Use of the latex chewing material or item will assist in keeping the teeth clean, promote healthy conditions of the teeth and gum by massaging the gums and providing exercise normally associated with mastication. In addition, the use of the latex chewing material will enhance the overall health and hygiene of the oral cavity by stimulating saliva secretions thereby decreasing the potential for bad breath.

1 Claim, 1 Drawing Sheet

INTERNATIONAL NON-STICK CHEWING MATERIAL

BACKGROUND OF THE INVENTION

FIELD OF THE INVENTION

The present invention generally relates to an international chewable material or item and more specifically to chewing material or items constructed of non-stick material such as latex rubber or the like. In one embodiment of the invention, the latex rubber chewing material is constructed to simulate the size and shape of a stick of conventional chewing gum. The latex material will not deteriorate when being chewed and while not intended to be ingested, it is constructed of non-toxic material and is not harmful if swallowed. The latex chewing material will not stick to any surface or any other item. The material is not water soluble and is sugar free and salt free. Use of the latex chewing material or item will assist in keeping the teeth clean, promote healthy conditions of the teeth and gum by massaging the gums and providing exercise normally associated with mastication. In addition, the use of the latex chewing material will enhance the overall health and hygiene of the oral cavity by stimulating saliva secretions thereby decreasing the potential for bad breath.

INFORMATION DISCLOSURE STATEMENT

Various types of chewing gums have been developed and have received considerable commercial success. Chewing gums are provided with various flavoring agents, sugar in some instances, and other additives to enhance the taste and other characteristics. However, the basic ingredients of chewing gum include chicle and other insoluble materials which, after being chewed, are quite sticky which causes a disposal problem. Chewing gum that has been chewed is frequently disposed of by placement under ledges and other downwardly exposed surfaces which creates an unsightly and unhealthy condition. If previously chewed gum is disposed of on a sidewalk, street or similar surface, it frequently will stick to the shoesoles of a person walking in that area and thus can be tracked onto floor surfaces, carpets and the like. Also, the natural material forming the basic ingredients of chewing gum and the additives incorporated therein are, in some instances, believed to be the cause of increased incidences of dental caries.

SUMMARY OF THE INVENTION

An object of the present invention is to provide a chewing material or item constructed of pure latex rubber that is cured in a conventional manner and does not include any additives and is constructed generally in the shape of a stick of conventional chewing gum in which the item is a thin, generally rectangular stick capable of being distributed in a wrapper to maintain sanitary conditions and easily placed in the mouth for chewing or mastication without the chewing item emitting flavoring agents or other additive materials into the oral cavity.

Another object of the invention is to provide a chewing material or item in accordance with the preceding object constructed of pure latex rubber which will not stick to any surface or any other item thereby eliminating the problems which exist from conventional chewing gum becoming stuck to various surfaces with which it comes into contact.

A further object of the invention is to provide a latex chewing material or item that enables a user to chew the material or item to obtain benefit from such mastication to maintain alertness and reducing drowsiness or sleepiness without smoking cigarettes, tobacco and pipes, alcoholic beverages, pills and narcotics and the like which are frequently used for these purposes.

Still another object of the invention is to provide a chewing material or item constructed of cured, pure latex rubber which is extremely simple in construction, provided with an indefinite shelf life, effective in producing benefits derived from chewing or mastication, non-allergenic, devoid of additives, water insoluble, effective as a cleaning agent for teeth and breath resulting from increased saliva circulation and capable of coming into contact with surfaces without sticking to such surfaces.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
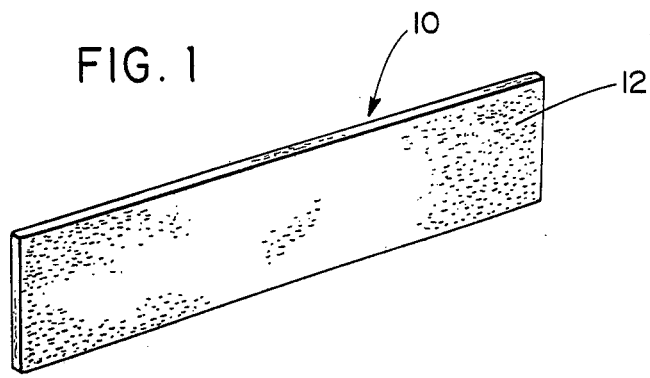
FIG. 1 is a perspective view of the chewing material or item of the present invention in the form of a thin, generally rectangular stick similar to a stick of conventional chewing gum.
Figure 2:
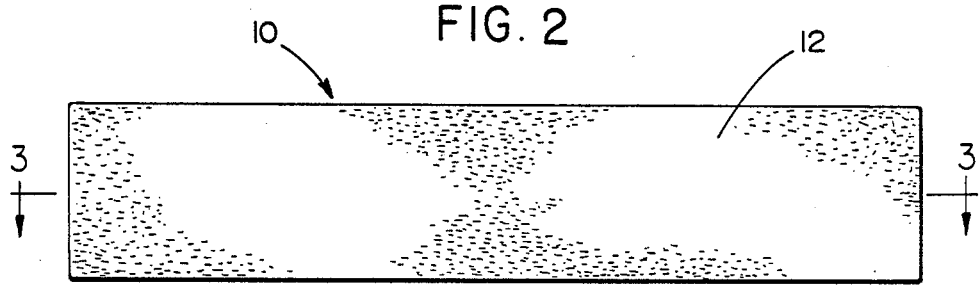
FIG. 2 is a plan view of the construction of FIG. 1.
Figure 3:
FIG. 3 is a longitudinal, sectional view along section line 3—3 on FIG. 2.

Referring now specifically to the drawings, the chewing material or item of the present invention is generally designated by the numeral 10 and includes an elongated, thin rectangular stick 12 having parallel top and bottom surfaces, parallel side edges and parallel end edges with the side and end edges being perpendicular to each other and perpendicular to the top and bottom surfaces. The stick of material 12 is homogenous and is constructed of pure latex rubber which is cured in a conventional manner and shaped and formed into the configuration illustrated in the drawings by conventional manufacturing techniques so that, in effect, a solid stick of pure latex rubber is provided with the latex rubber enabling the stick of material to be folded, rolled or otherwise shaped to easily place it in the mouth and chew it in a conventional manner. The chewing operation does not deteriorate the stick of chewing material in that it will maintain its flexibility, resiliency, shape and size. It will not emit or discharge any flavoring materials, sugar or any other additive into the mouth since no such materials have been incorporated into the latex rubber from which the stick 12 was constructed. The chewing or mastication tends to increase saliva secretions, massages the gums and other areas of the oral cavity and tends to relieve nervous tensions, stress and the like which enables the user to maintain alertness which is necessary when performing various duties when alertness is critical, such as operating vehicles, performing various manipulative operations and the like. By utilizing a conventional curing or vulcanizing process, the latex rubber stick 12 may be provided with any degree of flexibility and resiliency and with substantially any degree of penetration by the teeth thereby assuring that the stick of latex material will not deteriorate. The chewing material may be packaged in a striped or other decorative package in a manner similar to conventional chewing gum or candies in order to enhance marketability of the product. Use of the product enables a person to more successfully resist the use of narcotics, alcohol, tobacco (including smoking cigarettes, cigars and pipes as well as chewing tobacco) and reduces depression, anxiety and stress especially by users who may be operating a vehicle, walking or the like in which unusual concentration requirements may exist. In addition to latex rubber discussed above, the chewing material may be selected from materials such as foam plastic, natural sponge, various synthetic rubber materials, various plastics, fabric constructed from synthetic fibers, fabric constructed from natural fibers, silicone, fabric impregnated with silicone and nuts of various types including coconut combined with various additives and coca combined with various materials.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. A chewing material consisting of a body of flexible, resilient, non-toxic, water-insoluble, sugar-free, salt-free cured latex rubber adapted to be positioned in the oral cavity and chewed without deterioration for an extended period of time, said latex rubber being non-adhering by to surfaces in the oral cavity and externally of the oral cavity, said body of latex rubber being an elongated, thin, rectangular stick similar in shape, size and weight to a stick of conventional chewing gum with the flexibility and resiliency enabling the stick to be inserted into the oral cavity and folded, rolled and otherwise manipulated during mastication without deterioration from the mastication.

* * * * *